US012002081B2

(12) United States Patent
Orsita et al.

(10) Patent No.: US 12,002,081 B2
(45) Date of Patent: Jun. 4, 2024

(54) SYSTEM FOR GENERATING PRODUCT RECOMMENDATIONS USING BIOMETRIC DATA

(71) Applicant: L'OREAL, Paris (FR)

(72) Inventors: Fred Orsita, Clark, NJ (US); Jennifer Lee, Clark, NJ (US); Shelby Stewart, Clark, NJ (US)

(73) Assignee: L'OREAL, Paris (FR)

( * ) Notice: Subject to any disclaimer, the term of this patent is extended or adjusted under 35 U.S.C. 154(b) by 272 days.

(21) Appl. No.: 17/364,310

(22) Filed: Jun. 30, 2021

(65) Prior Publication Data

US 2021/0406982 A1 Dec. 30, 2021

Related U.S. Application Data

(60) Provisional application No. 63/065,220, filed on Aug. 13, 2020, provisional application No. 63/046,440, filed on Jun. 30, 2020.

(51) Int. Cl.
*G06Q 30/00* (2023.01)
*A61B 5/00* (2006.01)
(Continued)

(52) U.S. Cl.
CPC ......... *G06Q 30/0631* (2013.01); *A61B 5/381* (2021.01); *A61B 5/384* (2021.01); *A61B 5/6898* (2013.01); *A61B 2503/12* (2013.01)

(58) Field of Classification Search
CPC .. G06Q 30/06–08; A61B 5/381; A61B 5/384; A61B 5/6898
See application file for complete search history.

(56) References Cited

U.S. PATENT DOCUMENTS

| 3,978,847 | A | * | 9/1976 | Fehmi | ................... | A61B 5/369 |
| | | | | | | 600/545 |
| 2008/0065468 | A1 | * | 3/2008 | Berg | ..................... | G06Q 30/02 |
| | | | | | | 705/7.32 |

(Continued)

FOREIGN PATENT DOCUMENTS

JP 2011513851 A 4/2011

OTHER PUBLICATIONS

Search Report and Written Opinion dated Apr. 29, 2021, issued in corresponding French Application No. 2009180, filed Sep. 10, 2020, 6 pages.

(Continued)

*Primary Examiner* — Ethan D Civan
(74) *Attorney, Agent, or Firm* — CHRISTENSEN O'CONNOR JOHNSON KINDNESS PLLC

(57) ABSTRACT

Systems and methods for facilitating product preferences and/or product recommendations are disclosed. Biometric data of the subject are taken into account by the systems and methods in order to determine product preferences and/or product recommendations. Other factors of the subject, although optional, may be also taken into account while determining product preferences and/or product recommendations for a subject. These product preferences or recommendations can be presented to the subject, either automatically via a display device or with assistance from a product consultant. To obtain the biometric data, the subject will be exposed to a number of stimuli, such as fragrance/scent stimuli. Biometric data will then be collected from the subject based on her response to this fragrance/scent stimuli. In some examples, the collected biometric data relates to a subject's event-related potential (ERP)—the measured brain response that is the direct result of a specific sensory, cognitive, or motor event.

20 Claims, 11 Drawing Sheets

(51) Int. Cl.
    *A61B 5/381*     (2021.01)
    *A61B 5/384*     (2021.01)
    *G06Q 30/0601*     (2023.01)

(56) References Cited

U.S. PATENT DOCUMENTS

2017/0083927 A1    3/2017    Niedziela et al.
2018/0089739 A1*    3/2018    Cecchi ............... G06Q 30/0631

OTHER PUBLICATIONS

International Search Report and Written Opinion of the International Searching Authority dated Nov. 15, 2021, issued in corresponding International Application No. PCT/US2021/039970, filed Jun. 30, 2021, 10 pages.

Office Action mailed Jan. 29, 2024, issued in corresponding Japanese Application No. 2022-580979, filed Jun. 30, 2021, 12 pages.

\* cited by examiner

SYSTEM FOR GENERATING PRODUCT RECOMMENDATIONS USING BIOMETRIC DATA

CROSS-REFERENCES TO RELATED APPLICATIONS

This application claims the benefit of U.S. Provisional Application No. 63/046,440, filed Jun. 30, 2020, U.S. Provisional Application No. 63/065,220, filed Aug. 13, 2020, and French Application No. 2009180, filed Sep. 10, 2020, the disclosures of which are incorporated herein in their entirety.

FIELD OF THE DISCLOSURE

Embodiments of the present disclosures relate generally to the use of biometric data as an aid in product recommendations and/or selection. In some embodiments, the biometric data is utilized to determine product preferences of a user. In some of these embodiments, product preferences are used to aid in product recommendations and/or selection.

SUMMARY OF THE DISCLOSURE

Systems and methods for facilitating product preferences and/or product recommendations are disclosed herein. In embodiments described below, biometric data of the subject are taken into account by the systems and methods in order to determine product preferences and/or product recommendations. In some embodiments, other factors of the subject, although optional, may be also taken into account while determining product preferences and/or product recommendations for a subject. These product preferences or recommendations can be presented to the subject, either automatically via a display device or with assistance from a product consultant.

In some embodiments, to obtain the biometric data, the subject will be exposed to a number of stimuli, such as fragrance/scent stimuli. Biometric data will then be collected from the subject based on her response to this fragrance/scent stimuli. In some embodiments, the collected biometric data relates to a subject's event-related potential (ERP)—the measured brain response that is the direct result of a specific sensory, cognitive, or motor event.

For example, in some embodiments, the systems and methods detect an event-related potential based on the response to an olfactory stimulus. In that regard, the system and methods detect a real-time cognitive process associated with an olfactory stimulus, detect a real-time event-related potential associated with a response to one or more fragrance accords, detect voltage fluctuations indicative of a response to an olfactory stimulus or detect a postsynaptic potential based on a response to an olfactory stimulus.

In accordance with an aspect of the present disclosure, a system is provided, which in an embodiment comprises a plurality of sensors configured to sense an event-related potential of a subject based on a response to an olfactory stimulus, and one or more engines configured to: receive the event-related potential of a subject as EEG signals; process the EEG signals to generate EEG data; and generate a product recommendation based at least on said EEG data.

In some embodiments, the one or more engines are housed in a mobile computing device.

In some embodiments, the generated EEG data is represented as an image.

In some embodiments, the image includes an electroencephalograph (EEG) image or a brain activity map.

In some embodiments, the one or more engines are further configured to generate preferred characteristic parameters of the olfactory stimulus based on the EEG data and to generate the product recommendation based on the preferred characteristic parameters.

In some embodiments, the one or more engines are configured to determine a product recommendation by comparing data indictive of the generated preferred characteristic parameters to product data accessible by the one or more engines.

In some embodiments, the olfactory stimulus is a fragrance and wherein the data indictive of the generated preferred characteristic parameters includes a fragrance profile.

In some embodiments, the fragrance profile is presented to the subject as the product recommendation.

In some embodiments, the generated preferred characteristic parameters represent notes of the fragrance. In some embodiments, the product recommendation is generated by comparing the fragrance profile with a set of fragrance profiles representing, respectively, a set of fragrances, the set of fragrance profiles accessible by the one or more engines.

In some embodiments, the one or more engines includes processing circuitry configured to: detect a real-time cognitive process associated with an olfactory stimulus; detect a real-time event-related potential associated with a response to one or more fragrance accords; detect voltage fluctuations indicative of a response to an olfactory stimulus or detect a postsynaptic potential based on a response to an olfactory stimulus.

In some embodiments, the plurality of sensors and/or the one or more engines form a scent response unit includes one of: processing circuitry configured to detect a real-time cognitive process associated with an olfactory stimulus; processing circuitry configured to detect a real-time event-related potential associated with a response to one or more fragrance accords; processing circuitry configured to detect a postsynaptic potential based on a response to an olfactory stimulus; or processing circuitry configured to detect voltage fluctuations indicative of a response to an olfactory stimulus.

In some embodiments, the olfactory stimulus includes a scent. In some of these embodiments, the one or more engines form a perfume selection unit that includes one of the following: processing circuitry configured to generate one or more virtual instances of a fragrance subset based on at least one input associated with an electroencephalogram; processing circuitry configured to generate one or more instances of a degree of desirability score or a likeability measure; processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

In accordance with another aspect of the present disclosure, a system is provided that comprises a scent response unit and a perfume selection unit. In some embodiments, the scent response unit includes circuitry, such as processing circuitry, configured to detect an event-related potential based on a response to an olfactory stimulus. In some embodiments, the perfume selection unit includes circuitry, such as processing circuitry, configured to generate one or more virtual instances of a fragrance subset based on at least one input associated with the event-related potential.

In some embodiments, the scent response unit includes one of: processing circuitry configured to detect a real-time cognitive process associated with an olfactory stimulus; processing circuitry configured to detect a real-time event-related potential associated with a response to one or more fragrance accords; processing circuitry configured to detect a postsynaptic potential based on a response to an olfactory stimulus; or processing circuitry configured to detect voltage fluctuations indicative of a response to an olfactory stimulus.

In some embodiments, the perfume selection unit further includes one of: processing circuitry configured to generate one or more virtual instances of a fragrance subset based on at least one input associated with an electroencephalogram; processing circuitry configured to generate one or more instances of a degree of desirability score or a likeability measure; processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

In accordance with another aspect of the present disclosure, a method is provided for recommending a product to a subject. In an embodiment, the method comprises obtaining biometric data of a subject based on exposure to an olfactory stimulus, analyzing the biometric data, and recommending a product to the subject based on at least the analyzed biometric data.

In some embodiments, recommending a product to the subject based on the analyzed biometric data includes either presenting a fragrance name to the subject or presenting a fragrance profile to the subject.

In some embodiments, the method further comprises obtaining questionnaire data of the subject indicative of a preference of a characteristic parameter of a product. In some embodiments, recommendation of the product to the subject is based on the analyzed biometric data and the questionnaire data.

In some embodiments, the olfactory stimulus is a scent, wherein the product is a perfume, and the biometric data is indictive of EEG data.

In some embodiments, recommending a product includes generating a fragrance profile based on the EEG data and presenting the fragrance profile to the subject.

In some embodiments, recommending a product includes generating a fragrance profile based on the EEG data, comparing the fragrance profile with a set of fragrance profiles representing, respectively, a set of fragrances to select a fragrance from the set of fragrances having a fragrance profile most similar to the generated fragrance profile, and presenting the selected fragrance to the subject.

In some embodiments, obtaining biometric data of a subject based on exposure to a stimulus includes obtaining biometric data from at least two EEG electrodes associated with the front left (F7) lobe and the front right (F8) lobe of the subject.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
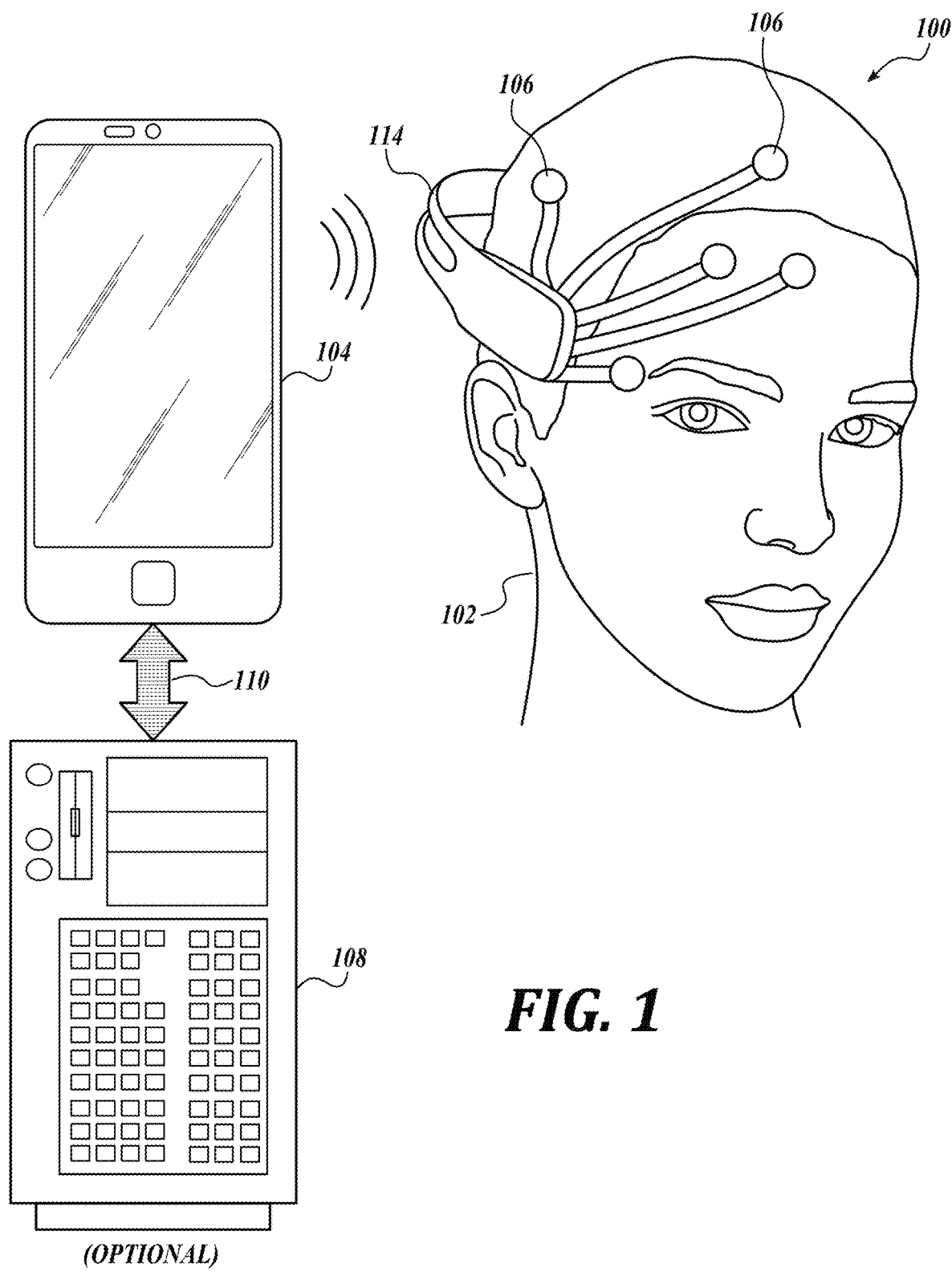
FIG. 1 is a schematic diagram that illustrates a non-limiting example of a system for generating and providing product, such as fragrance, recommendations to a subject according to an aspect of the present disclosure.

In order to provide recommendations for cosmetics, most existing techniques merely attempt to directly discern a subject's product preferences. Some techniques may attempt to determine a subject's product preferences based on the subject's stated preferences for a characteristic of the product, such as smell, color, finish, feel, etc. However, this technique produces sub-optimal recommendations, at least because only explicitly stated subject preferences are taken into account. Even in the presence of explicitly stated subject preferences, other factors (e.g., physical reactions (subconscious or conscious), personality traits, etc.), may also influence what products a given subject will prefer.

In that regard, in some embodiments of the present disclosure, biometric data of the subject are taken into account while determining product preferences and/or product recommendations. In other embodiments, other factors of the subject, although optional, may be also taken into account while determining product preferences and/or product recommendations for a subject. These product preferences or recommendations are then presented to the subject, either automatically via a display device or with assistance from a product consultant.

The examples described throughout the disclosure relate to recommendations for a fragrance, such a perfume or cologne. It will be appreciated that the techniques and methodologies of the present disclosure transcend product types, and thus, can be used to provide recommendations to the subject for products other than fragrances.

In the examples described below, a subject will be exposed to a number of stimuli, such as fragrance/scent stimuli. Biometric data will then be collected from the subject based on her response to this fragrance/scent stimuli. In some embodiments, the collected biometric data relates to a subject's event-related potential (ERP)—the measured brain response that is the direct result of a specific sensory, cognitive, or motor event. With this biometric data, a computer-based system will, for example, recommend either a specific fragrance or will develop a fragrance profile from which a recommendation can be made with the assistance of, for example, a technician or fragrance consultant. In other embodiments, the computer-based system will use the biometric data in conjunction with optional data, such as data obtained from a questionnaire, historical purchase data of the subject, etc., in order to present a product recommendation to the subject.

In some embodiments described herein, fragrances/scents presented to the subject may include two or more notes of an accord. Generally, an accord is a scent made up of several perfume notes, ingredients, etc., that blend together to form a distinct fragrance. For example, an accord usually includes a number of notes. Notes are descriptors of scents that can be sensed, and include base notes, middle or heart notes, and top or head notes. These scent descriptors or notes are well known and widely use to describe the odor character (e.g., a characteristic parameter) of a fragrance.

Figure 8:
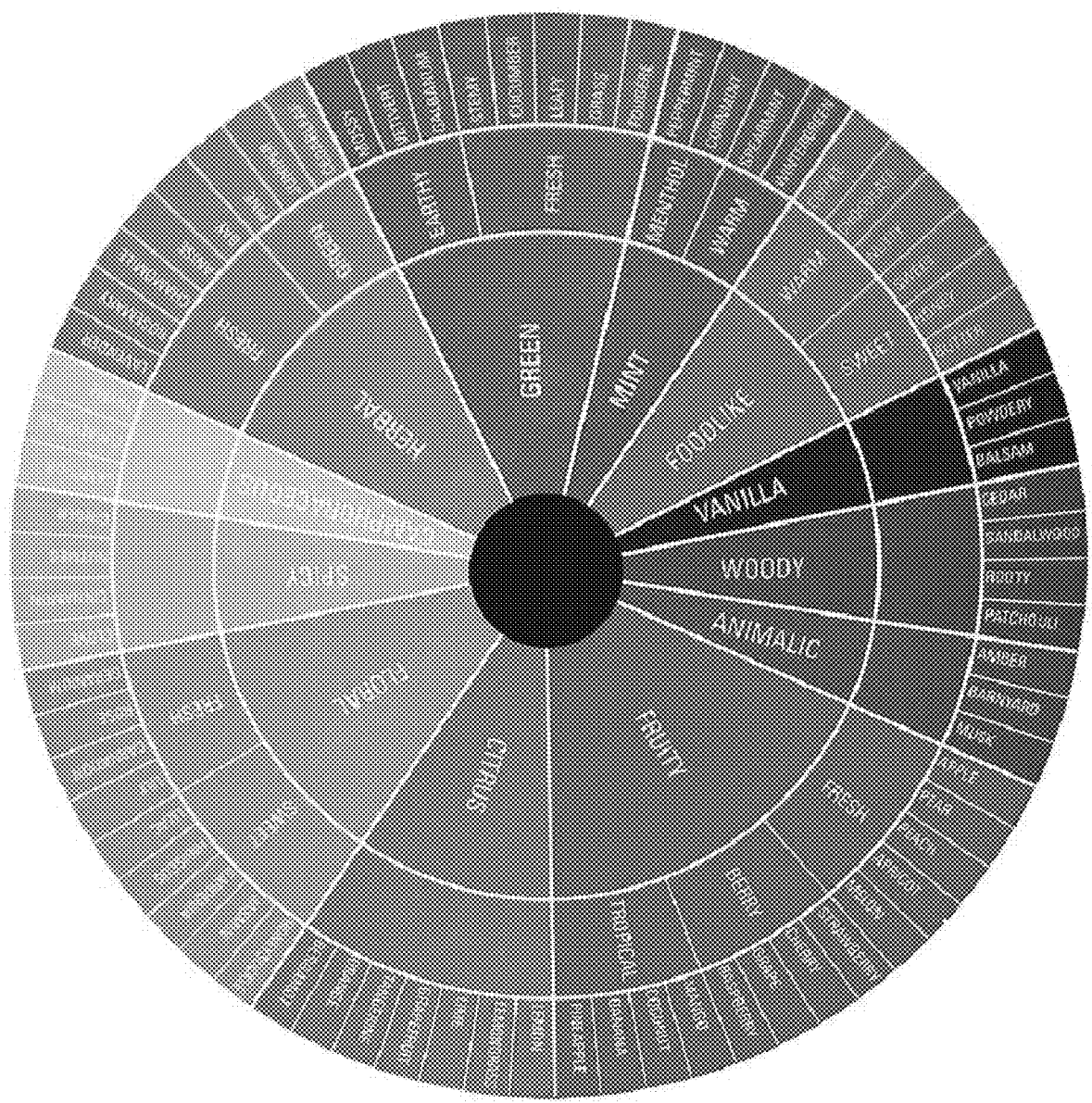
FIG. 8 is an example of a fragrance wheel.

Notes are typically chosen from fragrance families. Generally, fragrance families can be visually presented by a fragrance wheel. One example of a fragrance wheel is shown in FIG. 8. A fragrance wheel is a round diagram showing the inferred relationships among olfactory groups based upon similarities and differences in their odor. The groups bordering one another are implied to share common olfactory characteristics. Fragrance wheels are frequently used as a classification tool in oenology and perfumery.

Turning now to FIG. 1, there is shown a schematic diagram that illustrates a non-limiting example of a system 100 according to an aspect of the present disclosure. In the illustrated system, electrical activity of the brain of a subject 102 in the form of EEG signals is measured using physical collection devices 106, such as EEG sensors, in response to a subject's exposure to a stimulus, such as a fragrance. As shown, a plurality of physical collection devices 106 are placed on various regions of the subject's brain, for example via a suitable headset 114, in order to measure the electrical activity of the subject's brain. In some embodiments, as will be explained in more detail below, the regions of the brain associated with, for example, stimulation/relaxation and/or approach/avoidance are measured. Other regions of the brain may be additionally or alternatively measured for collecting EEG sensor data.

Still referring to FIG. 1, a mobile computing device 104 is coupled to the physical collection devices 106 in a wired or wireless manner to collect the EEG signals generated by the physical collection devices 106. In some embodiments, the mobile computing device 104 is used to process the collected signals, and based on the processed signals, determines a product recommendation to be presented to the subject 102. In other embodiments, the mobile computing device 104 develops a fragrance profile based on the processed signals, from which a recommendation can be made with the assistance of, for example, a technician or fragrance consultant.

Figure 9:
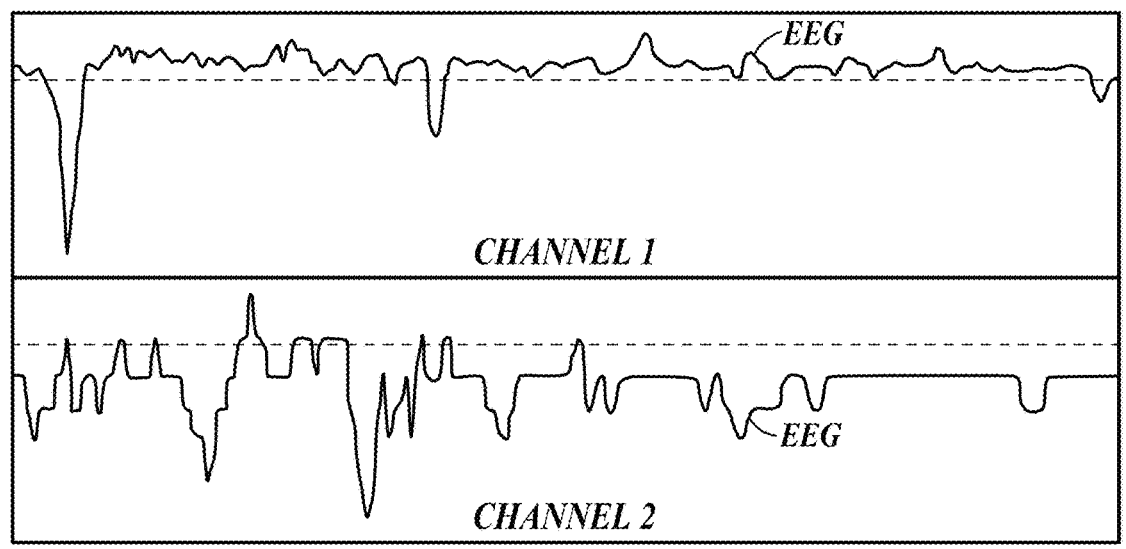
FIG. 9 is one example of an electroencephalograph generated as a result of processing collected EEG signals in accordance with the present disclosure.
Figure 10:
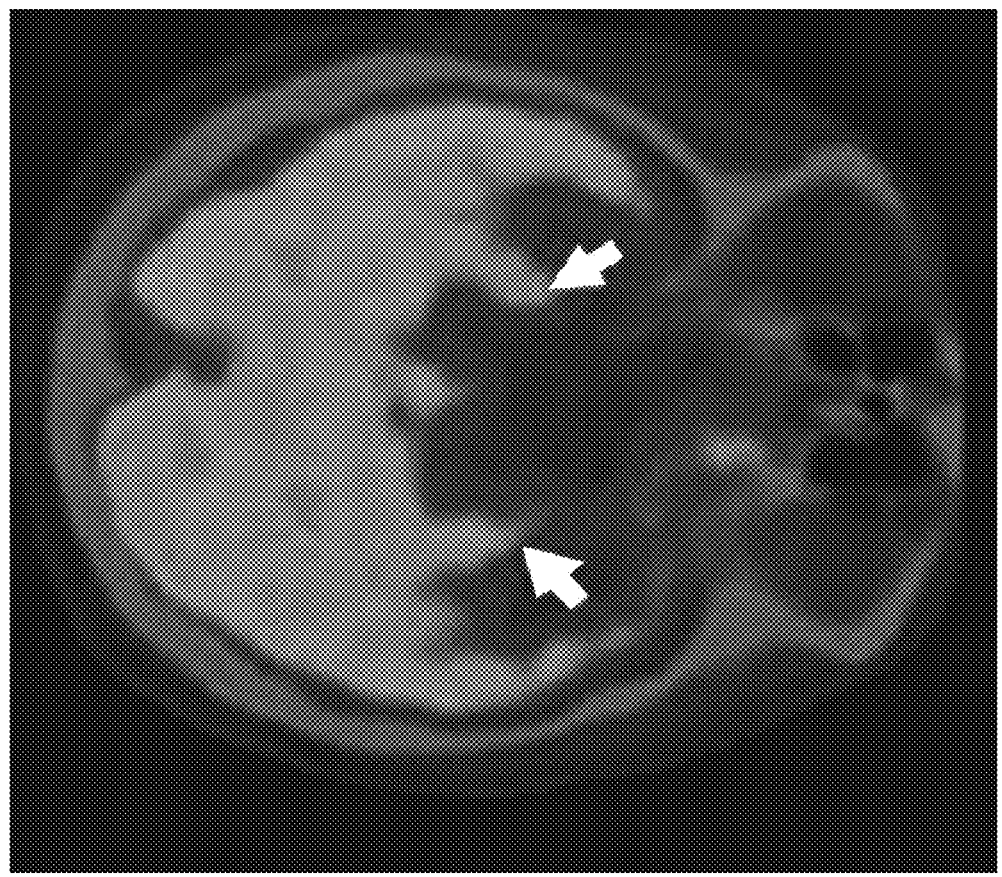
FIG. 10 is one example of a brain activity map generated as a result of processing collected EEG signals in accordance with the present disclosure.

In an embodiment, processing the collected EEG signals includes generating an electroencephalograph, such as the example shown in FIG. 9. In other embodiments, processing the collected EEG signals includes generating a brain activity map, such as the example shown in FIG. 10. The electroencephalograph and/or the brain map can then be used by the mobile computing device 104 to recommend a product for the subject or present a fragrance profile that can aid the subject in product selection. Of course, the mobile computing device 104 can utilize the collected EEG signals in other ways, including via non-graphical processing techniques, in order to provide a product recommendation to the subject.

The mobile computing device 104 in other embodiments may transmit the EEG signals (processed or not) as EEG data to an optional server computing device 108 via a network 110. In some embodiments, the network 110 may include any suitable wireless communication technology (including but not limited to Wi-Fi, WiMAX, Bluetooth, 2G, 3G, 4G, 5G, and LTE), wired communication technology (including but not limited to Ethernet, USB, and FireWire), or combinations thereof.

With the EEG data received from the mobile computing device 104, the server computing device 108 may respond back to the mobile computing device 104 with a product recommendation to be presented to the subject 102. In other embodiments, the server computing device 108 may develop a fragrance profile from the EEG data. The fragrance profile can then be transmitted to the mobile computing device 104. Once received by the mobile computing device 104, a recommendation can be made with the assistance of, for example, a technician or fragrance consultant. Of course, in some embodiments, the server computing device 108 can access via the network 110 a cloud based computer processing system (not shown) to augment its processing, analyzing, generating, etc., capabilities.

In some embodiments, the server computing device 108 processes the EEG data and generates an electroencephalograph and/or a brain map. The electroencephalograph and/or brain map can then be used by server computing device 108 to provide a product recommendation to the mobile computing device 104 for presentation to the subject 102. Alternatively, the generated electroencephalograph and/or brain map data is transmitted to the mobile computing device 104 for use by the mobile computing device 104 for providing a product recommendation to the subject 102.

In some embodiments, the mobile computing device 104 may also be used to present an optional questionnaire to the subject 102. The questionnaire may include questions that allow preferences of the subject 102 to be determined. In some embodiments, the questionnaire may also allow at least one personality trait to be determined. For example, in some embodiments, a personality trait can be correlated to one or more fragrance preferences, etc.

In some embodiments, the questionnaire can be served to the mobile computing device 104 by the optional server computing system 108 for presentation to the subject 102. In other embodiments, the mobile computing device 104 can generate and present the questionnaire to the subject.

In some embodiments, the responses to the questionnaire are received and processed locally by the mobile computing device 104. In other embodiments, the responses received by the mobile computing device 104 are sent to the optional server computing system 108 for processing. Of course, in some embodiments, the server computing device 108 can access via the network 110 a cloud based computer processing system (not shown) to augment its processing capabilities.

In any case, processed responses to the questionnaire may be used by either the mobile computing device 104 or the server computing device 108 in conjunction with the EEG signals collected from the subject for providing, for example, a product recommendation.

Figure 11:
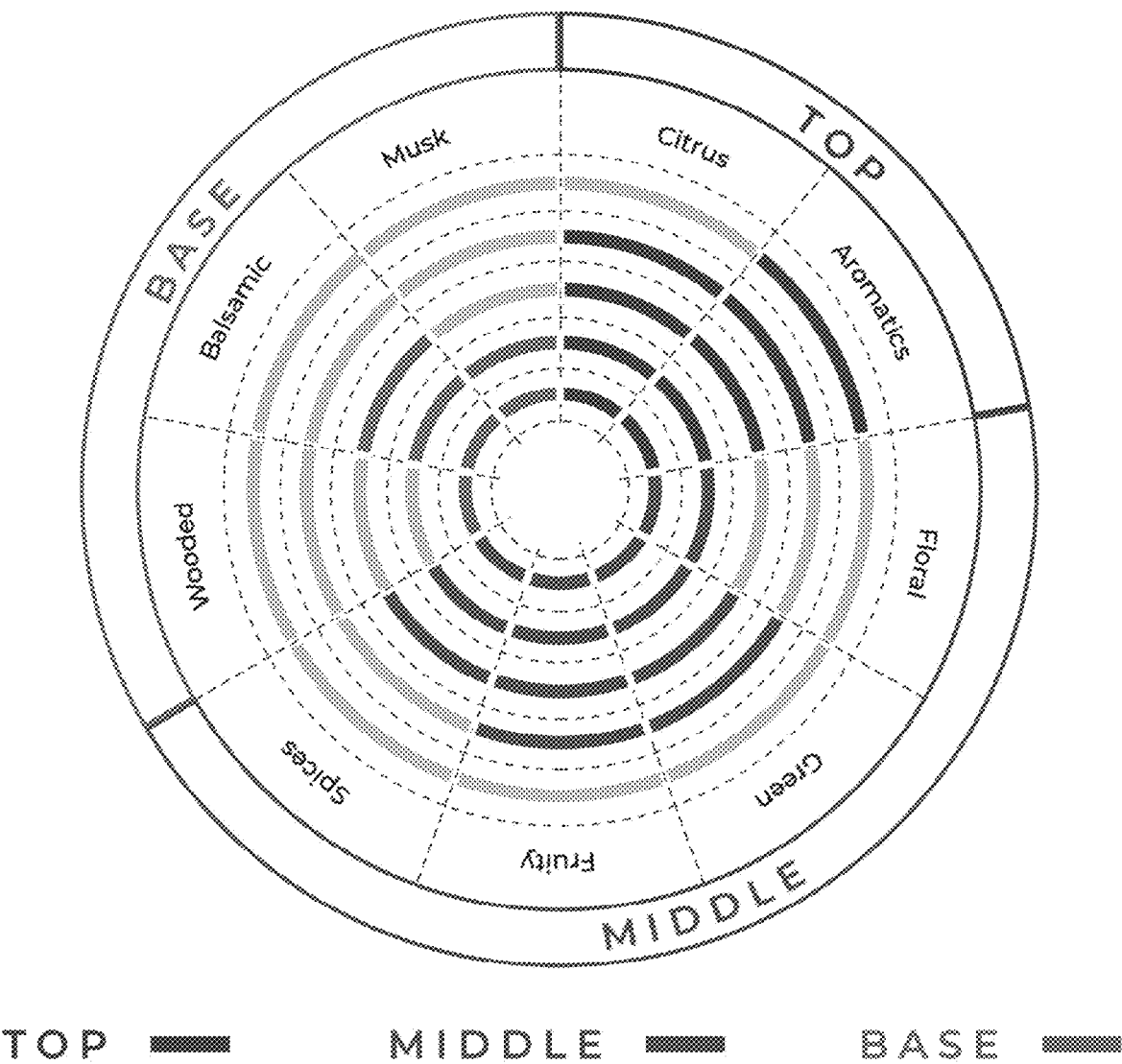
FIG. 11 is one example of a note diagram generated by the system and presented to the subject in accordance with an aspect of the present disclosure.

In some embodiments, the product recommendation may be provided to the subject 102 in a convenient, simple format. For example, the product recommendation can be a specific fragrance, e.g., identified by a tradename such as Trade Winds. Other information about the subject 102, such as scent preferences, a personality trait, prior fragrance purchases, etc., may be also presented to the subject. Additionally or alternatively, the product recommendation may take the form of a fragrance profile. The fragrance profile can be presented as a word-based description or visually depicted as a note diagram. One example of a note diagram generated by the system 100 and presented to the subject 102 is shown in FIG. 11. With the word-based description or the note diagram, a fragrance having a high probability of enjoyment by the subject can be selected, either independently or with the assistance of a fragrance consultant.

Figure 2:
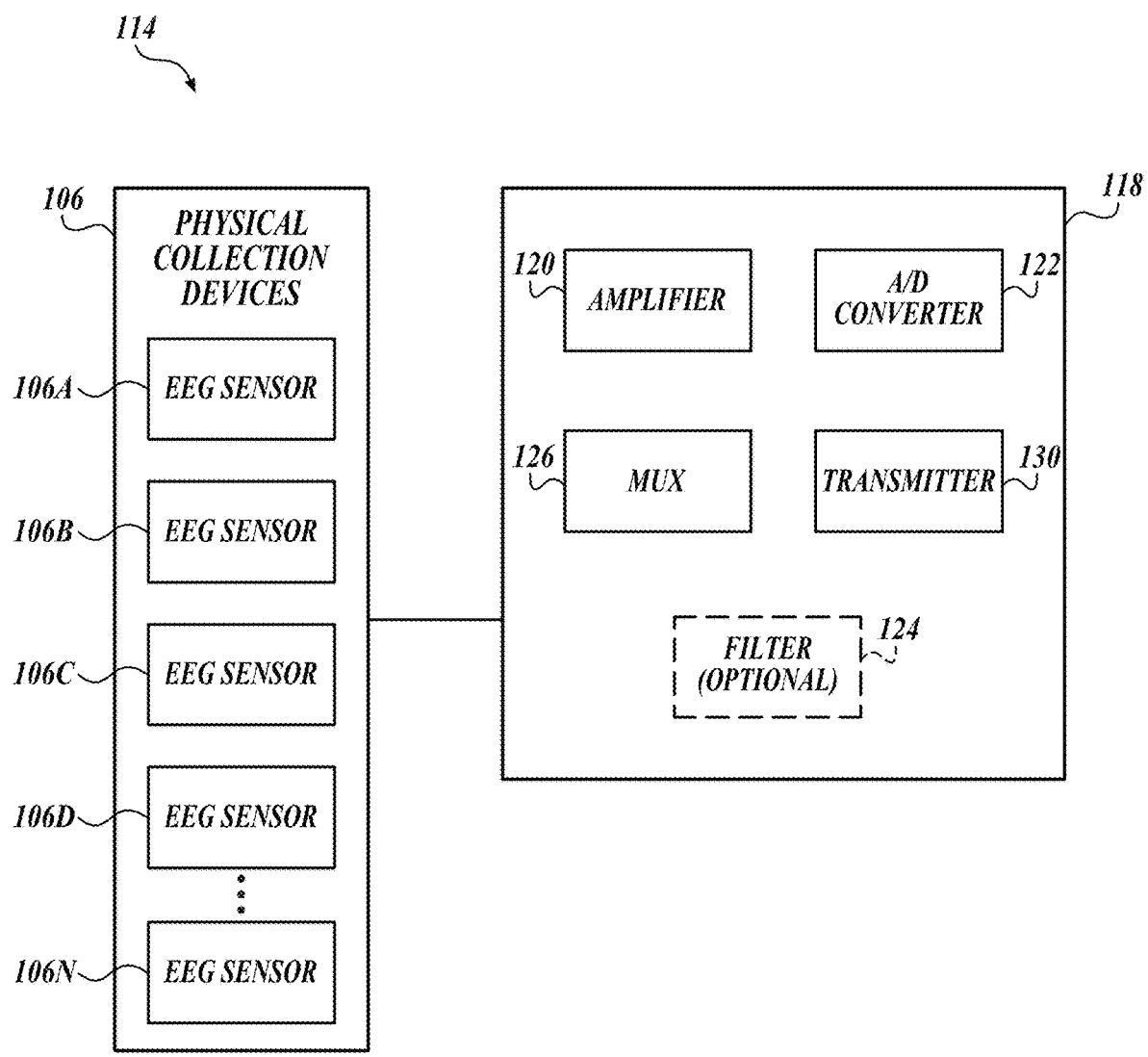
FIG. 2 depicts one example of a headset suitable for use in the system of FIG. 1.

FIG. 2 is a block diagram that illustrates various components of a non-limiting example of a headset 114 according to an aspect of the present disclosure. The headset 114 supports a number of physical collection devices 106 in the form of EEG sensors ("EEG sensors 106") and a process and transmit circuit 118. Generally, voltage changes occur from ionic current within and between neurons of the brain. The EEG sensors 106, sometimes referred to as EEG electrodes, are configured to measure these voltage changes in the subject's brain as EEG signals. The EEG signals measured by the EEG sensors 106 can be suitably processed for transmission to the mobile computing device 104 for storage, data processing and/or analysis, etc. For example, the EEG signals in some embodiments are amplified by an amplifier 120 and digitized by an A/D converter 122 prior to arrival at transmitter 130. In some embodiments, the EEG signals can be filtered in the analog domain prior to conversion by the A/D converter 122 or in the digital domain after conversion by the A/D converter 122 via one or more filters 124. In some embodiments, the filtered (optional) signals are sent to a multiplexer (MUX) 126 before transmission via the transmitter 130 to the mobile computing device 104.

The EEG electrodes 106 are generally formed of an electrical conducting material, such a stainless steel, silver/silver chloride material (Ag/AgCl), etc. The EEG electrodes 106 can be of the wet type (e.g., used with an electrolytic gel material as a conductor between the skin and the electrode) or of the dry type (e.g., an electrode of a single metal that acts as a conductor between the skin and the electrode). In some embodiments, a non-gel like material, such as saline, can be used as a conductive layer between the skin layer and the electrode.

In some embodiments, the EEG electrodes 106 can be active, in which the electrodes include a pre-amplification circuit immediately after the conductive material between the skin and the electrode. This allows the EEG signal to be amplified before additional noise may be added by the system in charge of capturing, processing or amplifying the EEG signal. Alternatively, the EEG electrodes can be passive in other embodiments. Passive electrodes do not include a pre-amplification circuit. Instead, passive electrodes simply extend the connection from the electrode's conductive material to the system components that process, amplify, and/or transmit the signal.

Figure 12:
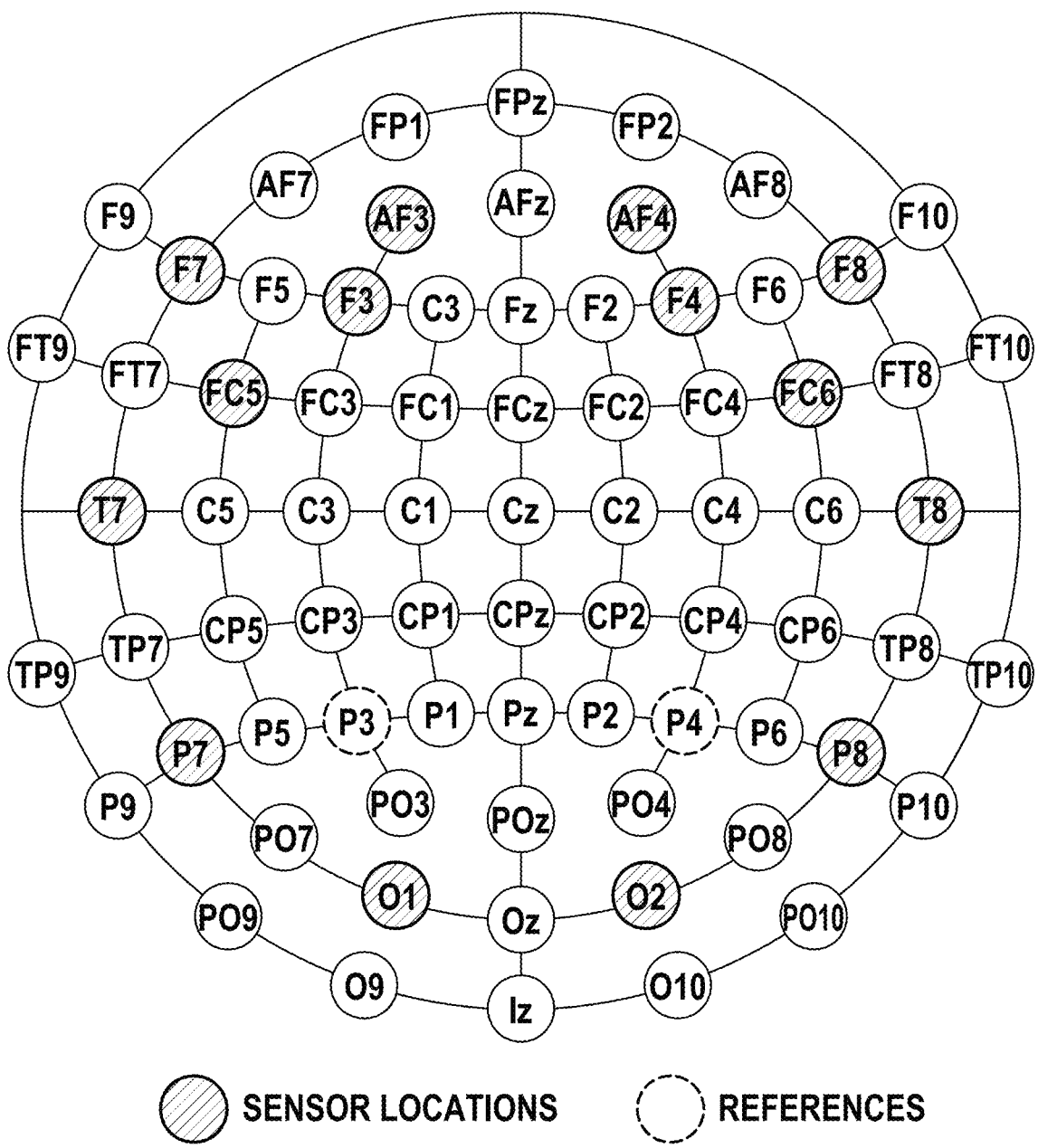
FIG. 12 is one example of an EEG electrode placement diagram in accordance with aspects of the present disclosure.

When placed on the subject's head, the EEG electrodes 106 of the headset 114 are generally aligned with various regions of the brain. Turning to FIG. 12, there is shown one example of an EEG electrode placement diagram in accordance with aspects of the present disclosure. It will be understood that several abbreviations in the diagram relate to the international 10-20 system, including "N" for nasion, "F" for frontal (e.g., in relation to the frontal lobe of a brain, which is the area located at the front of each cerebral hemisphere), "A" for ear lobe, "C" for center (e.g., in relation to a center area of the brain), "T" for temporal (e.g., in relation to the temporal lobe of the brain, which is located inferior and posterior to the frontal lobe at each cerebral hemisphere), "P" for parietal (e.g., in relation to the parietal lobe of the brain, which is located posterior to the frontal lobe), "O" for occipital (e.g., in relation to the occipital lobe of the brain, which is located at the back of the head), "I" for inion, and the subscript "z" for readings taken along the midline of the brain. The diagram of FIG. 11 also include abbreviations for AF, which is located between F and F, and FC, which is located between F and C.

As shown in the example of FIG. 12, EEG electrodes are positionally associated with the AF3, AF4, F3, F4, F7, F8, FC5, FC6, T7, T8, P7, P8, O1, and O2 regions of the subject's brain. In the embodiment shown, reference electrodes are located at P3 and P4, although other locations may be used. In some embodiments, only two electrodes are used, which are the front left (F7) and front right (F8) associated with approach (left brain activity) and avoidance (right brain activity), respectively. Of course, front left (F7) and front right (F8), along with any other combination of brain regions can be practiced with embodiments of the present disclosure. In some embodiments, the location of the EEG electrodes can be fixed by the headset. In other embodiments, the location of the EEG electrodes can be adjustable.

One non-limiting example of a headset 114 that outputs suitable signals for use by the system 100 is the EPOC+EEG Headset from Emotive. Other headsets that can be used are available from companies such as Brain Products, EGI, Cognionics, among others.

Figure 3:
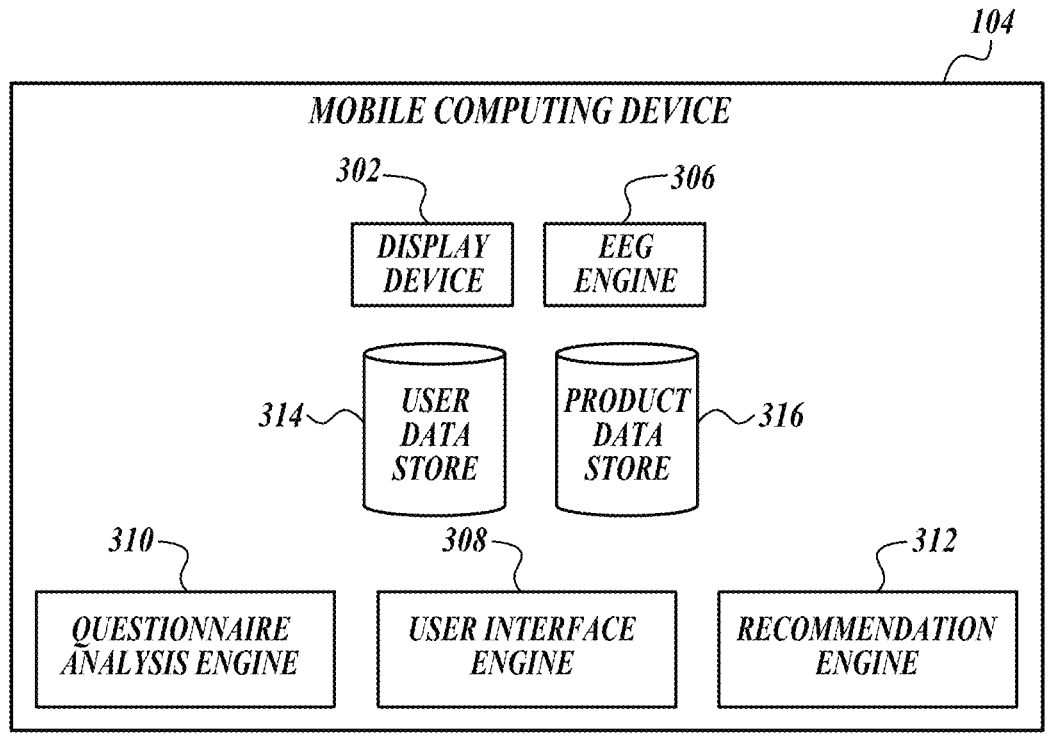
FIG. 3 is a block diagram that illustrates a non-limiting example of a mobile computing device suitable for use in the system of FIG. 1.

FIG. 3 is a block diagram that illustrates various components of a non-limiting example of a mobile computing device 104 according to an aspect of the present disclosure. The mobile computing device 104 is configured to collect information from a subject 102 that reflects brain activity based on exposure to one or more fragrances in, for example, a sequential order. In particular, the mobile computing device 104 is configured to receive EEG signals from one or more EEG sensors 106 for processing, recordation, transmission (optional) and/or analysis (optional). In some embodiments, the mobile computing device 104 is configured to receive EEG signals from the transmitter 130 of the headset 114 (See FIG. 2).

In some embodiments, the mobile computing device 104 processes the EEG signals for use in determining a product recommendation for the subject 102. In other embodiments, as will be described in more detail below, the EEG signals (processed or not) are transmitted as EEG data to the optional server computing system 108 via the network 110 for processing and/or generating a product recommendation, etc. In either case, the mobile computing device 104 can then present the product recommendation to the subject 102, or to a cosmetic consultant that is assisting the subject 102. In some embodiments, generating a product recommendation can be the identification of a specific product (e.g., a specific perfume/cologne). In other embodiments, generating a product recommendation can be information, such as a fragrance profile, that assists in the selection of a specific product or product family.

In some embodiments, the mobile computing device 104 may be a smartphone. In some embodiments, the mobile computing device 104 may be any other type of computing device having the illustrated components, including but not limited to a tablet computing device or a laptop computing device. In some embodiments, the mobile computing device 104 may not be mobile, but may instead be a stationary computing device such as a desktop computing device or computer kiosk. In some embodiments, the illustrated components of the mobile computing device 104 may be within a single housing. In some embodiments, the illustrated components of the mobile computing device 104 may be in separate housings that are communicatively coupled through wired or wireless connections. The mobile computing device 104 also includes other components that are not illustrated in FIG. 3, including but not limited to one or more processor circuits (referred generally as processors), a non-transitory computer-readable medium, a power source, and one or more network communication interfaces.

In order to implement some (or all) of the technology and methodology set forth herein, the mobile computing device 104 includes, in some embodiments for example, a display device 302, an EEG engine 306, a user interface engine 308, an optional questionnaire analysis engine 310, a recommendation engine 312, a user datastore 314 and a product datastore 316. Each of these components will be described in turn.

In some embodiments, the display device 302 is any suitable type of display device, including but not limited to an LED display, an OLED display, or an LCD display, that is capable of presenting interfaces to the subject 102. As will be described in more detail below, such interfaces include a questionnaire, a product recommendation, etc., to be presented to the subject 102. In some embodiments, the display device 302 may include an integrated touch-sensitive portion that accepts input from the subject 102.

In some embodiments, the EEG engine 306 is configured to collect EEG signals from the EEG sensors 106, process the EEG signals, and record the EEG signals in a time-based manner as EEG data in the user datastore 314. In some embodiments, processing the EEG signals may include but is not limited to converting, filtering, transforming, and/or the like. For example, in some embodiments, the EEG signals can be bandpass filtered to suitably pass signals in, for example, the alpha and/or beta frequency range. In some embodiments, the EEG engine 306 is also configured to process the signals in order to generate an electroencephalograph, such as the example shown in FIG. 9, and/or a brain activity map, such as the example shown in FIG. 10.

In some embodiments, the user interface engine 308 is configured to present a user interface on the display device 302. In some embodiments, the user interface engine 308 is configured to present a product recommendation, such as a name of a product or a fragrance profile to the user 102. In some embodiments, the user interface engine 308 may be configured to present visualizations of the EEG data as either an electroencephalograph or a brain activity map on the display device 302.

Figure 13:
FIG. 13 illustrates an example of a question, depicting one or more scenes, that is generated by the user interface engine and presented to the subject.

In some embodiments, the user interface engine 308 may be optionally configured to present on the display device 302 at least one questionnaire to the subject 102 for collecting information from the subject 102. In some embodiments, the questionnaire aims to collect information that may be relevant to the characteristic parameters of the fragrances to which the subject was or will be exposed. For example, the questionnaire may ask via a series of true/false or multiple choice questions that may elicit preferences to certain head, middle, or base notes. For example, one question of the questionnaire, which is shown in FIG. 13, may present to the subject a number of pictures depicting scenes, such as the beach, the forest, etc., to elicit a response to which depicted scene is associated with a preferred fragrance of the subject. In another question of the questionnaire, the subject may be asked whether they prefer feminine, masculine or unisex scents. In yet another question of the questionnaire, the subject may be asked whether they prefer the scent to be perceivable, subtle, complimentary or strong. In yet another question of the questionnaire, the subject may be asked to enter her preferred fragrances, including the most recently purchased fragrance. Some or all of the collected data can be stored, for example, in the user data store 314.

In some embodiments, the questionnaire analysis engine 310 may be configured to receive responses to the questionnaire from the subject 102 via the user interface engine 308, and may determine at least one preference, e.g., scent preference, scent characteristic, etc., of the subject 102 based on one or more of the responses. For example, if the subject 102 chose the scene of the forest as preferred, the questionnaire analysis engine 310 may be configured to determine that the subject 102 prefers woody notes, as shown for example in the fragrance wheel of FIG. 8. In some embodiments, the questionnaire analysis engine 310 may be configured to compare the responses to data stored, for example, in the product datastore 316. In an embodiment, the questionnaire analysis engine 310 may be configured to determine at least one personality trait of the subject 102 based on one or more of the responses.

In some embodiments, the recommendation engine 312 may be configured to generate at least one product recommendation for the subject 102 based at least on the EEG data. In other embodiments, the recommendation engine 312 may be configured to generate at least one product recommendation for the subject 102 based at least on the EEG data and the optional questionnaire data. In some embodiments, the product recommendation is in the form of a specific product, such as Trade Winds branded perfume. In other embodiments, the product recommendation is in the form of a fragrance profile. In these embodiments, the fragrance profile can be presented as a word-based description, visually depicted as a note diagram, etc. In some embodiments, the recommendation engine 312 provides the product recommendation to be presented to the subject 102 via the display device 302.

For example, FIG. 11 is one example of a fragrance note diagram that can be generated by the recommendation engine 312 and presented to the subject 102. The note diagram depicts characteristic parameters of the fragrances preferred by the subject 102. As shown in FIG. 11, the note diagram depicts visually the top notes, the heart or middle notes, and optionally, the base notes, that are preferable to the subject. These notes are represented in a pattern that form a wheel, with bar segments indicating strength of preference. For example, regarding the top notes, aromatics is depicted as five (5) bars, which the subject prefers more than floral, which is depicted as one (1) bar. Similarly, regarding the middle notes, fruity is depicted as four (4) bars, which the subject prefers more than spices, which is depicted as three (3) bars. In addition to or in the alternative to the number of bars, the color of the bars may also indicate strength of enjoyment. In some embodiments of the note diagram, the strength values may be linear (i.e., two bars is twice as preferable as one bar, etc.) or non-linear, such as Logarithmic, exponential, etc.

In the diagram depicted in FIG. 11, this subject enjoys aromatics, and to a lesser extent citrus, in the top notes, green and fruity, and to a lesser extent spices, in the middle notes, and balsamic, and to a lesser extent musk or wooded, in the base notes. In some embodiments, this note diagram can be presented on the display device 302 via user interface engine 308. In some embodiments, the note diagram can be used by a fragrance consultant to recommend a product type or product line that corresponds to the note profile of the note diagram. In other embodiments, the note diagram can be used by the subject 102 to compare to a fragrance chart of one or more fragrance sellers. In yet other embodiments, the recommendation engine 312 can analyze, for example, the image of the note diagram or the underlying data used to generate the note diagram, and based on the analysis, automatically present a product recommendation to the subject 102. In this latter embodiment, the product recommendation can be based on product data accessed, for example, from the product datastore 316.

In some embodiments, the recommendation engine 312 employs one or more algorithms for analyzing the images (e.g., the electroencephalograph, the brain activity map, etc.) generated from the biometric data. Based on this analysis, one or more characteristic parameters of the fragrances preferred by the subject 102 can be determined. For example, in some embodiments, areas of the electroencephalograph or brain activity map associated with the F7 and F8 regions of the brain are analyzed for the presence of increased stimulus. Such an increased stimulus may represent whether the subject 102 enjoys or does not enjoy the fragrance being exposed to. Of course, other combinations of regions of the brain can be analyzed in various embodiments.

In some embodiments, the preferred characteristic parameters of the fragrance are determined based on the image(s) of the EEG data. For example, in some embodiments, image processing techniques are applied to the images in order to determine the preferred characteristic parameters of the fragrances. In some embodiments, the recommendation engine 312 may comprise or access an artificial neural network that is trained to determine the characteristic parameters based on the images. Of course, any other type of suitable machine learning technique and/or classical image processing technique may be performed in order to determine the preferred characteristic parameters of the fragrances exposed to the subject 102.

For example, in some embodiments, the recommendation engine 312 includes a machine learning model for assisting in determining the product recommendation. The machine learning model can be trained using, for example, images of electroencephalographs, brain activity maps, etc., of subjects exposed to known fragrances (with known characteristic parameters, such as note profiles) that resulted in enjoyment by the subject. In some embodiments, the images from known fragrances are used to create a set of supervised training data, and a machine learning model such as an artificial neural network may be trained with the training data using any suitable technique, including but not limited to gradient descent. The resulting machine learning model will accept an image from the EEG engine 306 as input, and will output either preferred characteristic parameters or a product recommendation that has a high probability of enjoyment by the subject 102. In some embodiments, the preferred characteristic parameters can be used to generate a fragrance profile, such as the note diagram of FIG. 11, of the subject 102.

Accordingly, with the knowledge of the preferred characteristic parameters of the fragrances determined from the EEG data, and/or the optional questionnaire data, the recommendation engine 312 is configured to determine an appropriate product stored in a product data store 316 that matches or is highly correlative to the preferred characteristic parameters determined by the system 100. For example, the recommendation engine 312 can compare the results to a product map, a look-up table, etc., stored in the product data store 316. The comparison can be based, for example, on a potential match confidence level.

In some embodiments, the mobile computing device 104 may also include a user data store 314, which is configured to store records for each subject 102 that uses the system 100. The records may include, for example, at least one fragrance product, at least one fragrance profile, responses to a questionnaire, at least one personality trait, at least one product recommendation, and/or other information collected or determined by the system 100. In an embodiment, feedback received from the subject 102 after having used the recommended product(s) may also be stored in the user data store 322 or forward to the product data store 316 in order to improve future product recommendations by the system 100.

Further details about the actions performed by each of these components are provided below.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof. In some embodiments, the engines can be implemented by one or more circuits, programmable processors, application specific integrated circuits (ASICs), programmable logic devices (PLDs) and/or field programmable logic devices (FPLDs), etc.

"Data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 4:
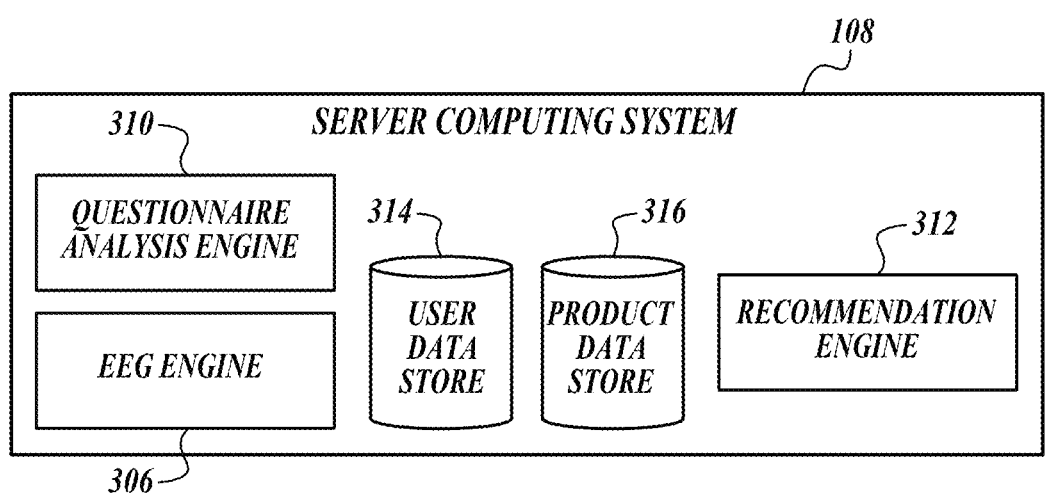
FIG. 4 is a block diagram that illustrates a non-limiting example of a server computing device suitable for use in the system of FIG. 1.

FIG. 4 is a block diagram that illustrates various components of a non-limiting example of an optional server computing system 108 according to an aspect of the present disclosure. In these embodiments, one or more functions of the mobile computing device set forth above can be additionally or alternatively carried out by the server computing device 108. For example, the fragrance preference information (e.g., scent preferences from, for example, biometric data (e.g., brain activity) from scent exposure and/or an optional questionnaire of the subject 102) collected by the mobile computing device 104 can be transmitted, with or without additionally processing (e.g., filtering, transforming, etc.) and/or storage, to the server computing system 108 via the network 110. In that regard, the server computing system 108 can include, for example, the EEG engine 306 (FIG. 3) for processing and storing the EEG signals and optionally generating an electroencephalograph, such as the example shown in FIG. 9 and/or a brain activity map, such as the example shown in FIG. 10.

In some embodiments, the server computing system 108 uses the information received from the mobile computing device 104 to determine a product recommendation to be used by the subject 102, and transmits the recommendation back to the mobile computing device 104 for presentation to the subject 102. In that regards, the server computing system 108 can additionally or alternatively include the questionnaire analysis engine 310, a recommendation engine 312, and/or a product data store 316, the functionality of which was described in detail above. In some embodiments, the server computing system 108 may also include the user data store 314.

Figure 5:
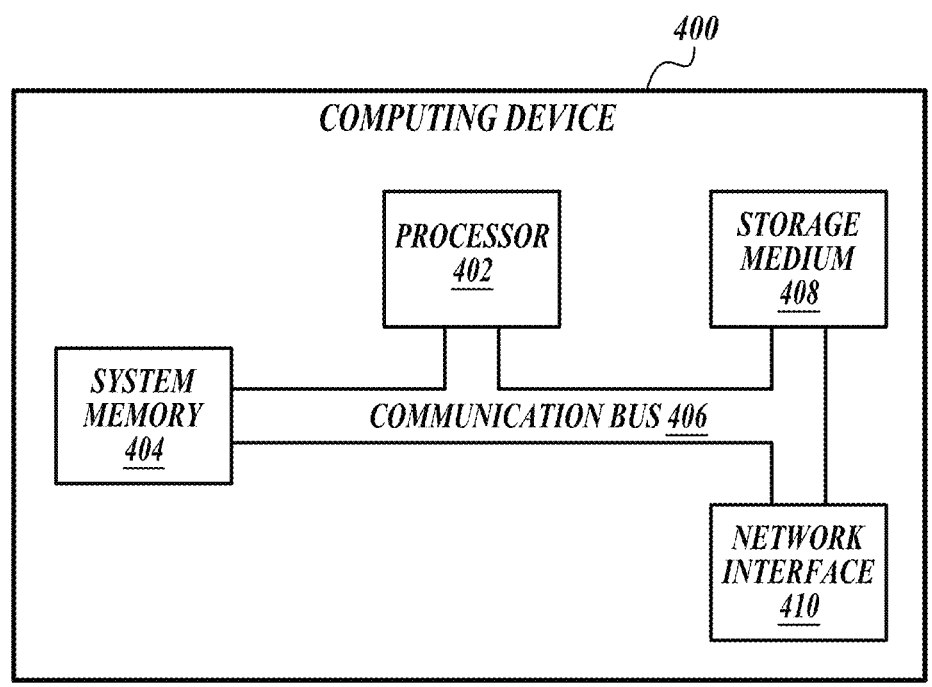
FIG. 5 is a block diagram that illustrates a non-limiting example of a computing device appropriate for use as a computing device with embodiments of the present disclosure.

FIG. 5 is a block diagram that illustrates aspects of a representative computing device 400 appropriate for use as a computing device of the present disclosure. While multiple different types of computing devices were discussed above, the representative computing device 400 describes various elements that are common to many different types of computing devices, such as the mobile computing device 104 and/or the server computing device 108. While FIG. 5 is described with reference to a computing device that is implemented as a device on a network, the description below is applicable to servers, personal computers, mobile phones, smart phones, tablet computers, computer kiosks, embedded computing devices, and other devices that may be used to implement portions of embodiments of the present disclosure. Moreover, those of ordinary skill in the art and others will recognize that the computing device 400 may be any one of any number of currently available or yet to be developed devices.

In its most basic configuration, the computing device 400 includes at least one processor 402 and a system memory 404 connected by a communication bus 406. Depending on the exact configuration and type of device, the system memory 404 may be volatile or nonvolatile memory, such as read only memory ("ROM"), random access memory ("RAM"), EEPROM, flash memory, or similar memory technology. Those of ordinary skill in the art and others will recognize that system memory 404 typically stores data and/or program modules that are immediately accessible to and/or currently being operated on by the processor 402. In this regard, the processor 402 may serve as a computational center of the computing device 400 by supporting the execution of instructions.

As further illustrated in FIG. 5, the computing device 400 may include a network interface 410 comprising one or more components for communicating with other devices over a network. Embodiments of the present disclosure may access basic services that utilize the network interface 410 to perform communications using common network protocols. The network interface 410 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 410 illustrated in FIG. 5 may represent one or more wireless interfaces or physical communication interfaces described and illustrated above with respect to particular components of the computing device 400.

In some embodiments in which the headset includes a multiplexer for combining multiple signal channels (one channel for each electrode), the network interface of the computing device, such as the mobile computing device 104, includes, for example, a demultiplexer implemented in hardware or in software to separate the received EEG signals into their respective channels. Alternatively, the EEG engine 306 can include such a demultiplexer. In these embodiments, the collected (e.g., received) EEG signals are passed through a demultiplexer in order for the mobile computing device 104 to process each channel of the EEG signals as EEG data.

In the exemplary embodiment depicted in FIG. 5, the computing device 400 also includes a storage medium 408. However, services may be accessed using a computing device that does not include means for persisting data to a local storage medium. Therefore, the storage medium 408 depicted in FIG. 5 is represented with a dashed line to indicate that the storage medium 408 is optional. In any event, the storage medium 408 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 404 and storage medium 408 depicted in FIG. 5 are merely examples of computer-readable media.

Suitable implementations of computing devices that include a processor circuit or processor 402, system memory 404, communication bus 406, storage medium 408, and network interface 410 are known and commercially available. For ease of illustration and because it is not important for an understanding of the claimed subject matter, FIG. 5 does not show some of the typical components of many computing devices. In this regard, the computing device 400 may include input devices, such as a keyboard, keypad, mouse, microphone, touch input device, touch screen, tablet, and/or the like. Such input devices may be coupled to the computing device 400 by wired or wireless connections including RF, infrared, serial, parallel, Bluetooth, Bluetooth low energy, USB, or other suitable connections protocols using wireless or physical connections. Similarly, the computing device 400 may also include output devices such as a display, speakers, printer, etc. Since these devices are well known in the art, they are not illustrated or described further herein.

In some embodiments, the plurality of sensors and/or the one or more engines form a scent response unit. In some embodiments, the scent response unit includes one of: processing circuitry configured to detect a real-time cognitive process associated with an olfactory stimulus; processing circuitry configured to detect a real-time event-related potential associated with a response to one or more fragrance accords; processing circuitry configured to detect a postsynaptic potential based on a response to an olfactory stimulus; or processing circuitry configured to detect voltage fluctuations indicative of a response to an olfactory stimulus.

In some embodiments, the one or more engines form a perfume selection unit that includes one of the following: processing circuitry configured to generate one or more virtual instances of a fragrance subset based on at least one input associated with an electroencephalogram; processing circuitry configured to generate one or more instances of a degree of desirability score or a likeability measure; processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

Figure 6:
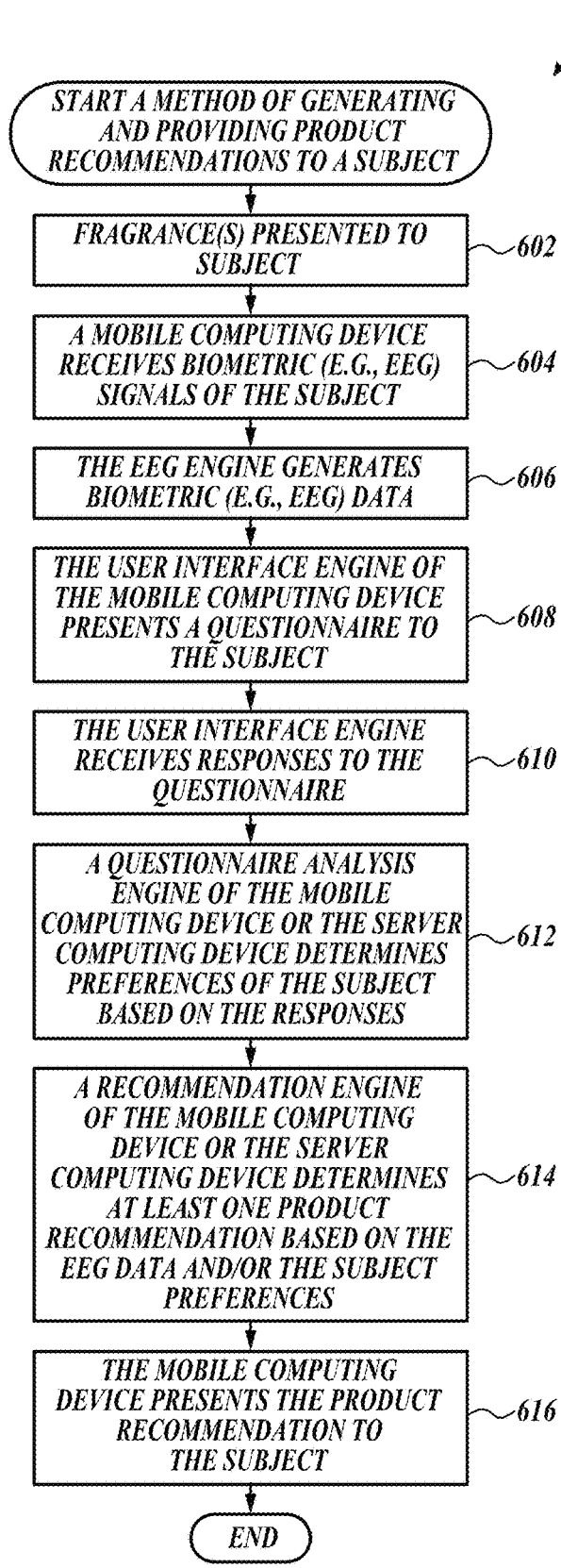
FIG. 6 is a flowchart that illustrates a non-limiting example of a method of generating and providing product recommendations to a subject according to an aspect of the present disclosure.

FIG. 6 is a flowchart that illustrates a non-limiting example of a method for generating and/or providing product recommendations to a subject according to one or more aspects of the present disclosure. The representative method, generally designated 600, will be described with references to one or more components of the system 100 depicted in FIGS. 1-5.

Prior to starting the method 600, one or more EEG sensors 106 are coupled to the head of the subject 102. In some embodiments, only two EEG sensors 106 are placed at the F7 and F8 regions of the subject's brain (with to without reference electrodes). In other embodiments, a headset 114 comprised of a number of EEG sensors 106 is placed on a head of a subject 102. In some of these embodiments, sensors 106 are located at the F7 and F8 regions in addition to other regions of the subject's brain. In some embodiments, reference electrodes can be positioned on the subject's head.

Once the sensors have been suitably associated with the head of a subject 102, the method can begin. From a start block, the method 600 proceeds to block 602, where the subject 102 is exposed to one or more fragrances. For example, the subject is exposed to a sequence of fragrances. The subject 102 is exposed to each fragrance for a period of time. In an embodiment, the period of time is about 45 seconds. Of course, shorter or longer periods of time can be employed. In other embodiments, the period of time is about five (5) minutes or longer. In some embodiment, the fragrances exposed to the subject include at least two fragrance notes, such as the top and middle notes.

The subject's reaction to the one or more fragrances is captured by the EEG sensors 106 and transmitted as EEG signals to the mobile computing device 104. In that regard, the mobile device 104 is coupled in communication with the EEG sensors 106 and receives the EEG (e.g., biometric) signals of the subject 102 at block 604.

At block 606, the EEG signals can then be processed by the EEG engine 306 to generate, for example, EEG data. In some embodiments, the EEG signals are processed by the EEG engine 306 residing on the mobile computing device 104. In other embodiments, the EEG signals are processed by the EEG engine 306 residing on the server computing device 108. In these or other embodiments, the EEG data is stored in the user datastore 314, either locally at the mobile computing device 104 or remotely at the server computing system 108.

In some embodiments, the actions performed at blocks 602, 604, 606 are repeated for each fragrance to be exposed to the subject 102. In other embodiments, the actions performed at blocks 602 and 604 can be performed for each fragrance prior to the actions performed at block 606. In an embodiment, the subject is exposed to four fragrances. Of course, a number of fragrances more or less than four can be used in embodiments of the present disclosure.

In one embodiment, a preselected set of fragrances are exposed to the subject 102. For example, the preselected set of fragrances can be the top four sellers in a company's line of fragrances. In other embodiments, as will be described in more detail with regard to FIG. 7 the reaction of the subject 102 to the preceding fragrance may be used by the system 100 to influence the choice of the subsequent fragrance(s) to be exposed to the subject 102. For example, the EEG data generated by the EEG engine 306 from exposure to a fragrance may be presented on the display device 302, for example, as an electroencephalograph or a brain activity map. With the aid of a fragrance consultant, the next fragrance can be chosen for exposure to the subject 102. Alternatively, the system can be configured to automatically choose the next fragrance to be presented to the subject based on the reaction of the subject to the previous fragrance(s).

In some embodiments, each fragrance exposed to the subject 102 includes at least two notes (e.g., a top and a middle note, two middle notes, a top and a base note, etc.). In some embodiments, each fragrance exposed to the subject 102 includes at least three notes (e.g., a top, a middle, and a base note (vertical accord), three middle notes (a horizontal accord), etc.) In any case, the characteristic parameters (e.g., top notes, middle notes, and/or base notes) of the fragrances exposed to the subject 102 are known and stored in the product datastore 316. In some embodiments, the characteristic parameters are stored, for example, as a note diagram.

In some embodiments, a user interface engine 308 of the mobile computing device 104 optionally presents a questionnaire to the subject 102 at bock 608. In some embodiments, the questionnaire may include questions that directly represent values for the subject 102. For example, the questionnaire may expressly ask the subject 102 to input a preference for fragrances, including specific product names, preferred notes, or other fragrance characteristics, such as whether the subject likes masculine, feminine or unisex fragrances, etc. In other embodiments, the user interface engine 308 presents one or more questions to the subject 102, the answers of which can be used to infer the subject preferences mentioned above or others.

At block 610, the user interface engine 308 receives responses to the questionnaire and transmits the responses to the questionnaire analysis engine 310 for processing. At block 612, the questionnaire analysis engine 310 determines one or more fragrance preferences based on the responses to the questionnaire. In some embodiments, the responses are processed by the questionnaire analysis engine 310 residing on the mobile computing device 104. In other embodiments, the responses are processed by the questionnaire analysis engine 310 residing on the server computing device 108. The user interface engine 308 may receive the responses via input into the user interface presented on the display device 302. The responses from the questionnaire and the results from processing the responses may be stored in the user data store 314. It will be appreciated that the actions performed at blocks 610 and 612 are also optional.

At block 614, a recommendation engine 312 determines a product recommendation based on at least the EEG data, and optionally, the preferences of the subject determined by the questionnaire engine 310. In doing so, the recommendation engine 312 may access data from the product data store 316. In some embodiments, the product recommendation is a particular product. In other embodiments, the product recommendation is a fragrance profile. In some embodiments, the product recommendation is determined by the recommendation engine 312 residing on the mobile computing device 104. In other embodiments, the product recommendation is determined by recommendation engine 312 residing on the server computing device 108.

At block 616, the product recommendation is presented to the subject. For example, in one embodiment in which a specific product is presented, the product recommendation can be displayed on the display device 302 along with, for example, a description (e.g., note profile) of the product, the price of the product, where the product can be purchased, etc. In other embodiments in which the product recommendation is in the form of a fragrance profile, the fragrance profile may be displayed to a fragrance consultant by the display device 302. With the assistance of the fragrance consultant, one or more products may be presented to the subject based on the fragrance profile.

The method 600 then proceeds to an end block and terminates.

Figure 7:
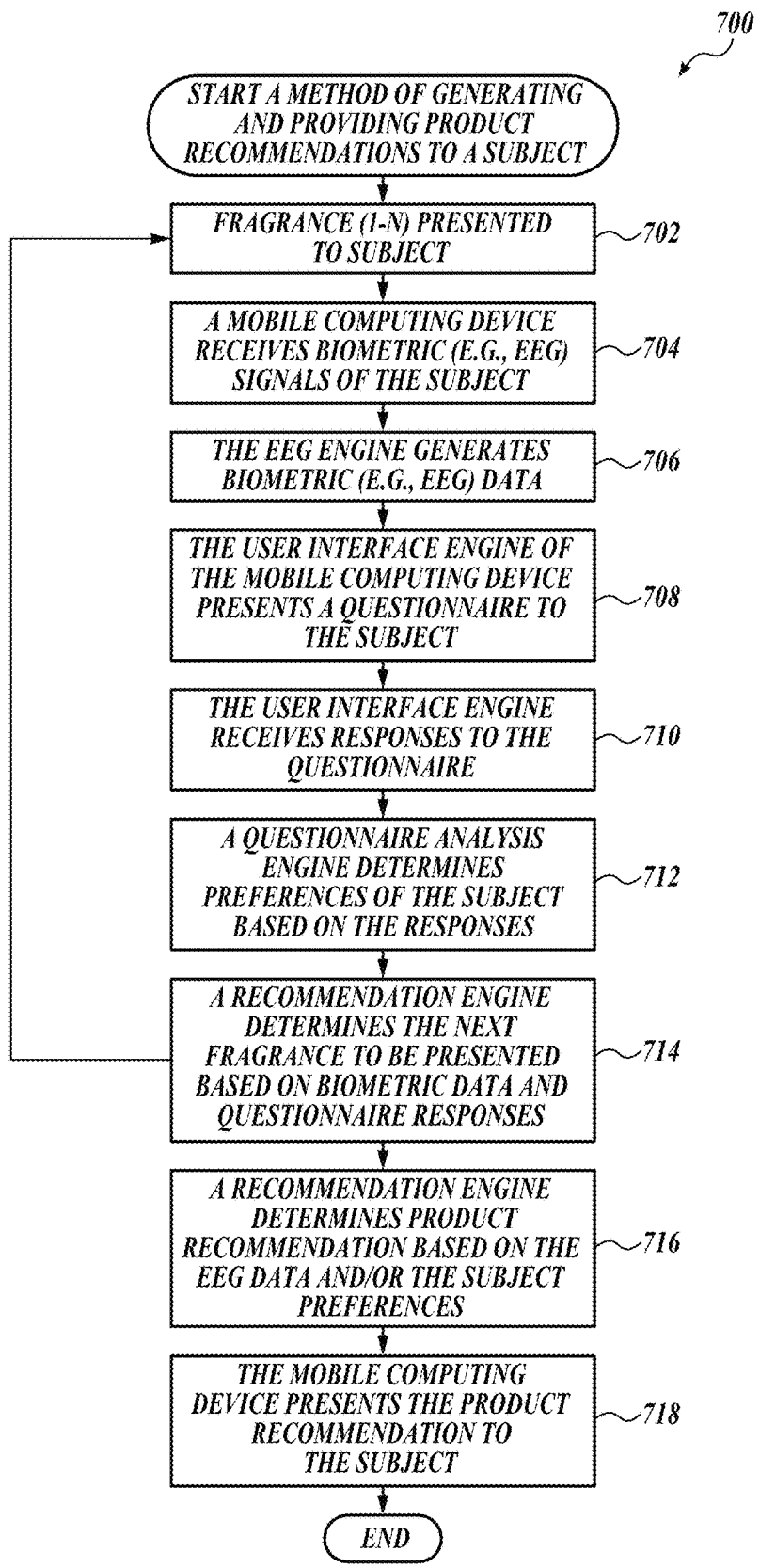
FIG. 7 is a flowchart that illustrates another non-limiting example of a method of generating and providing product recommendations to a subject according to an aspect of the present disclosure.

FIG. 7 is a flowchart that illustrates another non-limiting example of a method for generating and/or providing product recommendations to a subject according to one or more aspects of the present disclosure. The representative method, generally designated 700, will be described with references to one or more components of the system 100 depicted in FIGS. 1-5. The method 700 is substantially similar to the method 600 described above with reference to FIG. 6 except for the differences that will now be described.

In the embodiment of FIG. 7, the actions of blocks 702, 704 and 706 are performed sequentially for each fragrance to be exposed to the subject. In this embodiment, instead of the fragrances being preselected, the recommendation engine 312, or other engine of the system, determines the next fragrance to be presented to the subject 102 based on the biometric data generated from exposure to the preceding fragrance. In some embodiments, the recommendation engine 312 determines the next fragrance to be presented to the subject 102 based on the biometric data generated from exposure to the preceding fragrance and one or more responses from the questionnaire from block 708. Once all of the fragrances have been presented to the subject 102, the method 700 then proceeds to block 716, where the recommendation engine 312 determines a product recommendation.

In some embodiments, the first fragrance to be selected is determined based on one or more responses from the questionnaire. Accordingly, the questionnaire can be presented to the subject prior to any exposure to a fragrance.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Moreover, some of the method steps can be carried serially or in parallel, or in any order unless specifically expressed or understood in the context of other method steps.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

Throughout this specification, terms of art may be used. These terms are to take on their ordinary meaning in the art from which they come, unless specifically defined herein or the context of their use would clearly suggest otherwise.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A system, comprising:
   a plurality of electroencephalograph (EEG) electrodes configured to sense an event-related potential of a subject based on a response to an olfactory stimulus; and
   one or more engines configured to:
   receive the event-related potential of a subject as EEG signals generated by the EEG electrodes;
   process the EEG signals to generate EEG data; and
   generate a product recommendation based at least on said EEG data, wherein the product recommendation is generated by a recommendation engine that includes a machine learning model trained on a set of supervised training data comprising images of electroencephalographs or brain activity maps of subjects exposed to known fragrances.

2. The system of claim 1, wherein the one or more engines are housed in a mobile computing device.

3. The system of claim 1, wherein the generated EEG data is represented as an image.

4. The system of claim 3, wherein the image includes an electroencephalograph (EEG) image or a brain activity map.

5. The system of claim 1, wherein the one or more engines are further configured to generate preferred characteristic parameters of the olfactory stimulus based on the EEG data and to generate the product recommendation based on the preferred characteristic parameters.

6. The system of claim 5, wherein the one or more engines are configured to determine a product recommendation by comparing data indictive of the generated preferred characteristic parameters to product data accessible by the one or more engines.

7. The system of claim 5, wherein the olfactory stimulus is a fragrance and wherein the data indictive of the generated preferred characteristic parameters includes a fragrance profile.

8. The system of claim 7, wherein the fragrance profile is presented to the subject as the product recommendation.

9. The system of claim 7, wherein the generated preferred characteristic parameters represent notes of the fragrance, and wherein the product recommendation is generated by comparing the fragrance profile with a set of fragrance profiles representing, respectively, a set of fragrances, the set of fragrance profiles accessible by the one or more engines.

10. The system of claim 1, wherein the one or more engines are configured to detect the event-related potential based on the response to an olfactory stimulus includes processing circuitry configured to:
    detect a real-time cognitive process associated with an olfactory stimulus;
    detect a real-time event-related potential associated with a response to one or more fragrance accords;
    detect voltage fluctuations indicative of a response to an olfactory stimulus; or
    detect a postsynaptic potential based on a response to an olfactory stimulus.

11. The system of claim 1, further comprising:
    a perfume selection unit including processing circuitry configured to generate one or more virtual instances of a fragrance subset based on at least one input associated with the event-related potential.

12. The system of claim 11, wherein the perfume selection unit further includes one of:
    processing circuitry configured to generate one or more virtual instances of a fragrance subset based on at least one input associated with an electroencephalogram;
    processing circuitry configured to generate one or more instances of a degree of desirability score or a likeability measure;
    processing circuitry configured to generate one or more instances of a scent strength;
    processing circuitry configured to generate one or more instances of aromatic compound concertation; or
    processing circuitry configured to generate one or more instances of base notes, top notes or middle notes in a fragrance composition.

13. A method for recommending a product to a subject, comprising:
    obtaining biometric data in the form of event-related potential of a subject as electroencephalograph (EEG) signals generated by a plurality of EEG electrodes based on exposure to an olfactory stimulus;
    processing the EEG signals to generate EEG data; and
    generating a product recommendation based at least on the EEG data, wherein the product recommendation is generated by a recommendation engine that includes a machine learning model trained on a set of supervised training data comprising images of electroencephalographs or brain activity maps of subjects exposed to known fragrances.

14. The method of claim 13, wherein generating the product recommendation includes
    presenting a fragrance name to the subject; or
    presenting a fragrance profile to the subject.

15. The method of claim 13, further comprising
    obtaining questionnaire data of the subject indicative of a preference of a characteristic parameter of a product,
    wherein the product recommendation is further based on the questionnaire data.

16. The method of claim 13, wherein the product recommendation is a perfume recommendation.

17. The method of claim 16, wherein the product recommendation includes a fragrance profile based on the EEG data.

18. The method of claim 17 further comprising comparing the fragrance profile with a set of fragrance profiles representing, respectively, a set of fragrances to select a fragrance from the set of fragrances having a fragrance profile most similar to the generated fragrance profile, and presenting the selected fragrance to the subject.

19. The method of claim 14, wherein are positioned at a front left (F7) lobe and front right (F8) lobe of the subject and are configured to detect brain activity associated with approach and avoidance responsive to the exposure to the olfactory stimulus.

20. A non-transitory computer-readable medium having stored thereon instructions configured to cause a computer system to perform steps comprising:
    obtaining biometric data in the form of event-related potential of a subject as electroencephalograph (EEG) signals generated by a plurality of EEG electrodes based on exposure to an olfactory stimulus;
    processing the EEG signals to generate EEG data; and
    generating a product recommendation based at least on the EEG data, wherein the product recommendation is generated by a recommendation engine that includes a machine learning model trained on a set of supervised training data comprising images of electroencephalographs or brain activity maps of subjects exposed to known fragrances,
    wherein the EEG electrodes are positioned at a front left (F7) lobe and front right (F8) lobe of the subject and are configured to detect brain activity associated with approach and avoidance responsive to the exposure to the olfactory stimulus.

* * * * *

UNITED STATES PATENT AND TRADEMARK OFFICE
CERTIFICATE OF CORRECTION

| | | |
|---|---|---|
| PATENT NO. | : 12,002,081 B2 | Page 1 of 1 |
| APPLICATION NO. | : 17/364310 | |
| DATED | : June 4, 2024 | |
| INVENTOR(S) | : F. Orsita et al. | |

It is certified that error appears in the above-identified patent and that said Letters Patent is hereby corrected as shown below:

In the Claims

| Column | Line | |
|---|---|---|
| 20 | 35 | change "wherein are" to -- wherein the EEG electrodes are --. |

Signed and Sealed this
Third Day of February, 2026

John A. Squires
*Director of the United States Patent and Trademark Office*